(12) United States Patent
Rummakko et al.

(10) Patent No.: US 7,863,441 B2
(45) Date of Patent: Jan. 4, 2011

(54) PREPARATION OF QUETIAPINE

(75) Inventors: Petteri Rummakko, Espoo (FI); Soini Huhta, Espoo (FI); Arne Grumann, Kauniainen (FI)

(73) Assignee: Fermion Oy, Espoo (FI)

( * ) Notice: Subject to any disclaimer, the term of this patent is extended or adjusted under 35 U.S.C. 154(b) by 1024 days.

(21) Appl. No.: 10/572,409

(22) PCT Filed: Sep. 23, 2004

(86) PCT No.: PCT/FI2004/000560
§ 371 (c)(1),
(2), (4) Date: Jan. 16, 2007

(87) PCT Pub. No.: WO2005/028458
PCT Pub. Date: Mar. 31, 2005

(65) Prior Publication Data
US 2007/0111987 A1    May 17, 2007

Related U.S. Application Data

(60) Provisional application No. 60/504,981, filed on Sep. 23, 2003.

(51) Int. Cl.
*C07D 281/16*    (2006.01)
*C07D 295/18*    (2006.01)

(52) U.S. Cl. .................................................... 540/551
(58) Field of Classification Search ................ 540/551
See application file for complete search history.

(56) References Cited

U.S. PATENT DOCUMENTS

| 3,539,573 A | 11/1970 | Schmutz et al. |
| 2007/0111986 A1 | 5/2007 | Hilden et al. |

FOREIGN PATENT DOCUMENTS

| WO | WO-01/55125 A | 8/2001 |
| WO | WO-02/083624 A | 10/2002 |

OTHER PUBLICATIONS

Database Beilstein Crossfire Beilstein Institut Zur Foerderung Der Wissenschaften, Frankfurt, Main, DE; Citation No. 5562436 1988, XP002316545.

Warawa E J et al., Journal of Medicinal Chemistry, American Chemical Society. Washington, US, vol. 44, Feb. 1, 2001, pp. 372-389, XP002213291, ISSN: 0022-2623.

*Primary Examiner*—Brenda L Coleman
(74) *Attorney, Agent, or Firm*—Birch, Stewart, Kolasch & Birch, LLP

(57) ABSTRACT

The present invention discloses a process for the preparation of quetiapine, which comprises the ring closure of a compound of the formula shown below, as well as novel intermediates in the process.

5 Claims, No Drawings

PREPARATION OF QUETIAPINE

This application is the National Phase of PCT application PCT/FI2004/000560, filed Sep. 23, 2004 and claims priority under 35 U.S.C. 119(e) on U.S. Provisional Application Nos. 60/504,981 filed Sep. 23, 2003, all of which are hereby incorporated by reference.

The present invention is directed to a new method for the preparation of quetiapine. Further objects of the invention are novel intermediates useful in the process according to the invention.

BACKGROUND OF THE INVENTION 11-(4-[2-(2-hydroxyethoxy)ethyl]-1-piperazinyl]dibenzo[b,f]-1,4-thiazepine (I) is a well established drug substance known under the INN name quetiapine.

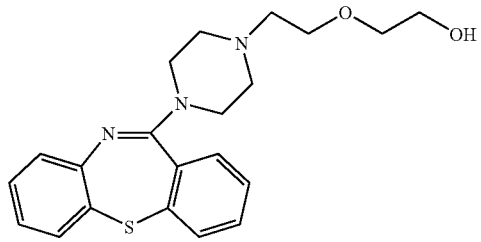

I

It is used as hemifumarate salt as an antipsychotic or neuroleptic.

Several methods for the preparation of quetiapine are known, as disclosed in e.g. GB 8607684, GB 8705574, and WO 01/55125. The known methods include reacting a halo derivative (e.g. iminochloride) of dibenzo[b,f][1,4]-thiazepin-11(10-H)-one with 1-(hydroxyethoxyethyl)piperazine; reacting the aforementioned halo derivative with piperazine and reacting the resulting intermediate with a halo ethoxyethanol; and reacting a haloethylpiperazinylthiazepine derivative with ethylene glycol.

SUMMARY OF THE INVENTION

The present invention is directed to a method for the preparation of the compound of formula I or a salt thereof

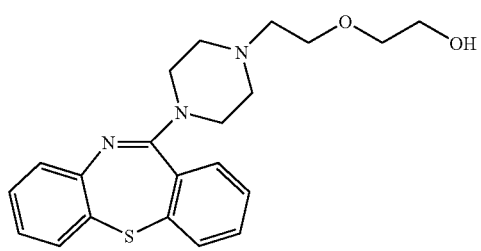

I by cyclization of a compound of formula II or a salt thereof

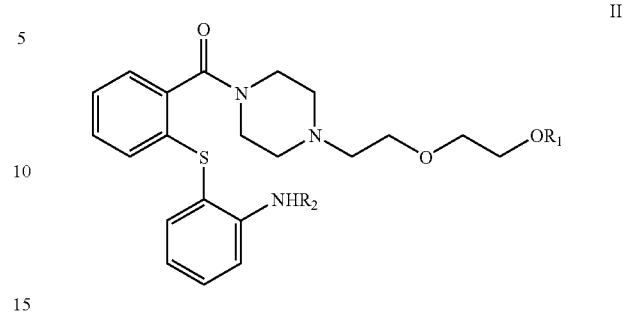

II wherein $R_1$ is a hydroxyl protecting group selected from the group consisting of acetyl, benzoyl, pivaloyl, benzyl, 4-methoxybenzyl, allyl, tetrahydropyranyl, silyl, alkyl carbonate, aryl carbonate, aralkyl carbonate, benzyl carbonate, allylsulfonyl, benzylsulfonyl, toluenesulfonyl and R2 is H or a suitable amino protecting group, e.g. acetyl, pivaloyl or benzyl to produce a compound of formula III or a salt thereof

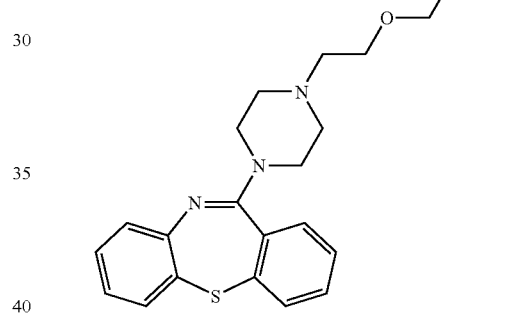

in which $R_1$ is defined as above, which on removal of $R_1$ yields compound I or a salt thereof.

The compound of formula I or a salt thereof can be further reacted to a pharmaceutically acceptable salt thereof, e.g. hemifumarate.

The inventors have surprisingly noticed that the thiazepine ring closure tales place in Vilsmeier reaction conditions even though both hydroxyl and aniline moiety are acetate protected. To the knowledge of the inventors this kind of reaction is previously unknown and offers a novel method for the preparation of quetiapine and other thiazepines.

Selective hydroxyl group protection of intermediate V is difficult to perform. For example, if acetylation is used, a mixture of mono O-acetate and diacetylated compounds is frequently obtained. The possibility of using the diacetylated compound in ring closure reaction step makes the whole process more easy to work. It is also possible to use mixtures of mono O-acetate and diacetate in the ring closure step.

The invention also includes the novel intermediate compounds II defined above and salts thereof, and further compounds of formula IV and salts thereof

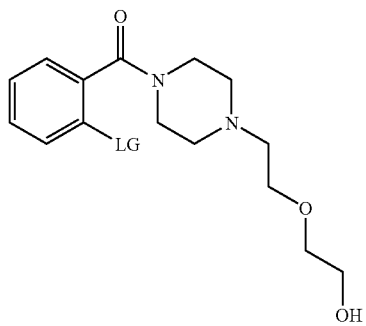

IV

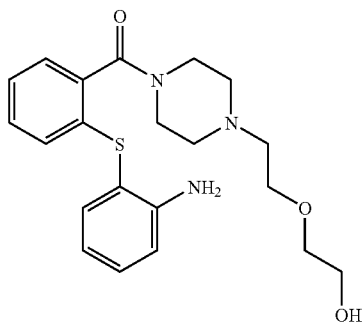

V wherein LG is a leaving group, e.g. halogen, diazonium, trifluoromethyl, O-trifluoromethane-sulfonyl, O-p-toluenesulfonyl or O-methanesulfonyl, preferably halogen or diazonium.

Compounds I to VII can also be used and prepared as suitable salts thereof, e.g as acetates or hydrochlorides.

DISCLOSURE OF THE INVENTION

According to the present invention, cyclization of compound II yields compound III, which on hydroxyl deprotection yields the target compound, quetiapine, which can be further reacted to a pharmaceutically acceptable salt, e.g. hemifumarate.

Preferably, the ring closure takes place under Vilsmeier conditions in the presence of a chlorinating agent and optionally in the presence of a strong tertiary amine base. Possible chlorinating agents include but are not limited to $POCl_3$, $SOCl_2$, $PCl_3$, $PCl_5$, $COCl_2$, and $(COCl)_2$; preferably, the reagent is $POCl_3$. The chlorinating agent may be used in large excess but preferably 4 to 5 molar equivalent is used. Possible bases include triethylamine, di-isopropylethylamine, DABCO, N,N-dimethylamine and triethylenediamine. The reagent can act as a solvent, but also a co-solvent selected e.g. from toluene, xylene, acetonitrile and chlorinated hydrocarbons can be used. Preferred co-solvents, if used, are toluene, acetonitrile and mixtures of these. Carboxylic acids, e.g. acetic acid, water, inorganic acids and alcohols can be used as beneficial additives in this reaction. The reaction temperature and the duration are dependent on the solvent used; advantageously reflux temperature or a temperature close thereto is used. For example, the temperature may be in the range 50-120° C. and the reaction time in the range of 0.5 to 6 h.

Compound III may be deprotected by saponification using a suitable base in an alcohol to give quetiapine. Preferably, the reaction takes place with aqueous alkali metal hydroxide in methanol, ethanol or 2-propanol. Quetiapine base can be converted to a pharmaceutically acceptable salt, e.g. hemifumarate by methods known in the art and purified further e.g. by crystallization from a suitable solvent.

$R_1$ and $R_2$ may be introduced individually or in one step by reaction of intermediate V or a salt thereof with one or more reagents reactive towards amino and/or hydroxyl groups.

According to a preferable embodiment of the present invention, compound II or a salt thereof is represented by the diacetyl compound VI or a salt thereof, which is obtained by acetylation of intermediate V or a salt thereof.

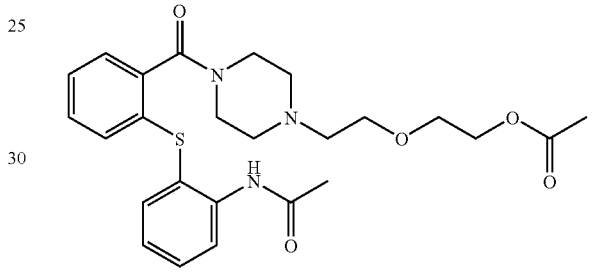

VI

According to another embodiment of the present invention, compound II or a salt thereof is represented by the mono-, i.e. O-acetylated compound VII or a salt thereof,

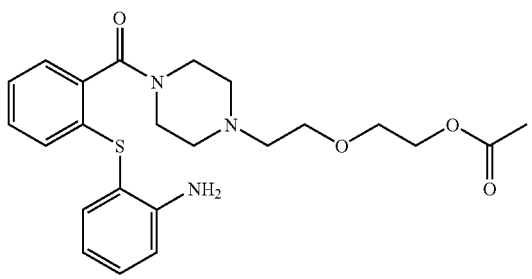

VII obtainable under non-exhaustive acetylation conditions. Acetylation may also result in a mixture of mono- and diacetylated product, which may be used in place of the pure intermediates.

Acetylation may be carried out in a mixture of acetic acid and acetic anhydride or acetyl chloride with or without cosolvent. Possible cosolvents include ethers, esters, aromatic hydrocarbons, chlorinated hydrocarbons, ketones and acetonitrile. The temperature may be in the range of 0-120° C. and the reaction time 1-20 h. If the diacetylated compound is prepared, acetylation reagent is used with 1 to 3 fold excess.

Intermediate V or a salt thereof may be obtained by coupling of 2-aminothiophenol with intermediate IV or a salt thereof, which can be used either isolated or a crude product from the reaction between compound of formula VIII or a salt thereof and 1-[2-(hydroxyethoxy)-ethyl]-piperazine.

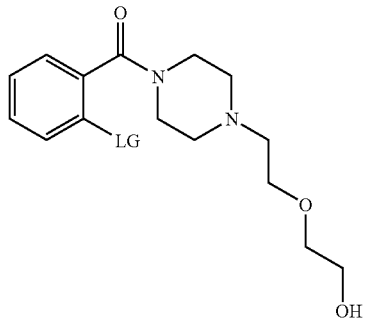

IV

LG represents a leaving group, e.g. halogen, diazonium, trifluoromethyl, O-p-toluenesulfonyl or O-methanesulfonyl. The reaction is carried out optionally in the presence of a metal catalyst, a base and a ligand compound in a solvent.

Useful metal catalysts include palladium, nickel and copper compounds. Preferable catalysts are copper iodide and copper bromide. Useful solvents include water, ionic liquids, alcohols, polyethylene glycol, N,N-dimethylformamide, toluene, acetonitrile and mixtures thereof. Preferably, the solvent is water or an alcohol or the mixture of these. The base present may be organic or inorganic; preferably, the base is potassium carbonate. The ligand compound may be a diol, a diamine, an aminoalcohol or EDTA. Preferably, if the ligand compound is used, it is ethylene glycol.

The reaction temperature and duration are dependent on the solvent used. For example, the temperature range may be 50-120° C. and the reaction time 1-20 h.

Intermediate IV may be prepared by reaction of 1-[2-(hydroxyethoxy)-ethyl]-piperazine with a compound of formula VIII

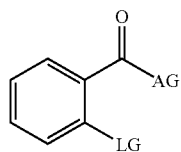

VIII wherein LG is defined as above and AG is a typical carboxylic acid activating group, e.g. halogen, alkyloxy, aryloxy, mixed aliphatic or aromatic anhydride, azide or carbodiimide.

The reaction may be carried out in the presence of a base. Possible solvents include water, aromatic hydrocarbons, chlorinated hydrocarbons, esters and ethers or their mixtures with water. Triethylamine, other tertiary amines or inorganic bases may be used. Preferably the reaction is carried out in water without a base. The reaction takes place in ambient temperature, but any temperature between 0-100° C. may be used.

The following examples merely illustrate the invention and they are not to be construed as limiting.

EXAMPLES

Example 1 a. {4-[2-(2-hydroxy-ethoxy)ethyl-piperazin-1-yl}-(2-iodophenyl)-methanone 2-iodobenzoic acid (20 g, 0.081 mol), toluene (20 ml) and thionyl chloride (30 ml, 0.41 mol) were charged into a reaction flask. The mixture was stirred and refluxed for 11 h. Toluene (40 ml) was added and the solvent and excess of thionylchloride were distilled off under reduced pressure. The process was repeated with 20 ml of toluene. The residue of 2-iodobenzoyl chloride was dissolved into THF (20 ml). 1-[2-(hydroxyethoxy)-ethyl]-piperazine (14.1 g, 0.081 mol), THF (100 ml), water (50 ml) and triethylamine (12.3 ml) were added into a reaction flask and stirred at icewater bath temperature. The previously prepared 2-iodobenzoyl chloride THF solution was slowly added to the reaction mixture. The temperature was kept below 20° C. during the addition. The reaction mixture was allowed to warm to room temperature and stirred 2 h at ambient temperature. 50 ml of water was added and THF was removed by distillation. The pH of the solution was checked and adjusted to 9-10. The water was extracted three times with dichloromethane (50 ml). The combined organic phase was evaporated yielding {4-[2-(2-hydroxy-ethoxy)ethyl-piperazin-1-yl}-(2-iodophenyl)-methanone as a yellowish oil, which was used without further purification. Yield 31 g.

$^1$H NMR (CDCl$_3$): 2.42 (1H, m), 2.63 (5H, m), 3.25 (2H, m), 3.59 (2H, m), 3.68 (4H, m), 3.90 (3H, m), 7.06 (1H, t), 7.18 (1H, d), 7.40 (1H, t), 7.83 (1H, d).

$^{13}$C NMR (CDCl$_3$): 41.3, 45.9, 46.6, 52.7, 53.4, 57.7, 61.9, 67.8, 72.4, 92.5, 127.0, 128.4, 130.2, 139.2, 142.1, 169.1.

b. 2-(2-amino-phenylsulfanyl)-phenyl-{4(2-(2-hydroxyethoxy)ethylpiperazin-1-yl}methanone {4-[2-(2-hydroxy-ethoxy)ethyl-piperazin-1-yl}-(2-iodophenyl)-methanone (10 g, 0.025 mol) was dissolved in isopropanol (50 ml) and ethylene glycol (2.5 ml). CuI (0.24 g, 5 mol %) and K$_2$CO$_3$ (6.9 g) were added to the reaction mixture. The reaction vessel was flushed with nitrogen, and 2-aminothiophenol (3.4 g, 0.028 mol) was added under a nitrogen atmosphere. The reaction mixture was refluxed overnight (12-18 h). Solid material was filtered off and the solvent was evaporated. The residue was dissolved in ethyl acetate (100 ml) and washed once with 1 M NaOH (25 ml). Water (100 ml) was added and the pH was adjusted to 5 with dilute acetic acid. The organic layer was washed once with water (50 ml) and the water phases were combined. The pH of the water was adjusted to 10-11 with 1 M NaOH and the basic water phase was extracted twice with ethyl acetate (100 ml). The combined organic phases were evaporated to afford [2-(2-amino-phenylsulfanyl)-phenyl-{4(2-(2-hydroxyethoxy)ethyl]piperazin-1-yl}methanone as a dark red oil, yield 8.8 g.

$^1$H NMR (CDCl$_3$): 2.51 (2H, s), 2.64 (4H, m), 3.36 (2H, m), 3.60-3.71 (6H, m), 3.90 (2H, s, broad), 4.46 (2H, s), 6.73 (2H, m), 6.94 (1H, m), 7.15-7.29 (4H, m), 7.45 (1H, d).

$^{13}$C NMR (CDCl$_3$): 41.4, 46.8, 52.9, 53.7, 57.8, 61.9, 67.8, 72.4, 113.8, 115.4, 118.2, 126.1, 126.4, 128.4, 129.5, 131.3, 133.9, 135.7, 137.4, 149.3, 168.5.

Steps a and b can also be performed in one pot without isolation of the intermediate made in step a.

c. [2-(2-acetamino-phenylsulfanyl)-phenyl]-{4(2-(2-acetoxyethoxy)ethyl]-piperazin-1-yl}methanone

[2-(2-amino-phenylsulfanyl)-phenyl]-{4(2-(2-hydroxy-ethoxy)ethyl]piperazin-1-yl}methanone (10.7 g, 0.027 mol) was dissolved in ethyl acetate (50 ml) and triethylamine (7.4 ml) was added into reaction mixture. Acetic anhydride (7.6 ml, 0.081 mol) was slowly added to the reaction mixture at room temperature. After 4 h, the reaction mixture was evaporated to give a dark blue oil which was dissolved in ethyl acetate (50 ml) and washed with 2×25 ml saturated $NaHCO_3$ solution and once with brine. The organic phase was evaporated to give a brown oil (10.9 g). The residue of [2-(2-acetamino-phenylsulfanyl)-phenyl]-{4(2-(2-acetoxyethoxy)ethyl]-piperazin-1-yl}methanone was used further without purification.

$^1$H NMR ($CDCl_3$): 2.04 (3H, s), 2.08 (3H, s), 2.49 (2H, m), 2.66 (4H, m), 3.29 (2H, s, broad), 3.66 (3H, m), 3.90 (1H, m), 4.21 (2 h, d), 7.07 (1H, t), 7.08-7.39 (3 h, m), 7.61 (1H, t), 7.63 (1H, d), 8.34 (1H, d), 8.80 (1H, s).
$^{13}$C NMR ($CDCl_3$): 21.0, 24.3, 41.7, 47.0, 53.1, 53.8, 63.4, 68.8, 69.0, 121.3, 122.2, 123.8, 126.1, 127.5, 130.0, 130.6, 131.5, 132.8, 136.3, 137.0, 140.2, 168.7, 169.6, 170.9.

d. 11-(4-[2-(2-acetyloxyethoxy)ethyl]-1-piperazinyl]dibenzo[b,f]-1,4-thiazepine

[2-(2-acetamino-phenylsulfanyl)-phenyl-{4(2-(2-acetoxyethoxy)ethyl]piperazin-1-yl}methanone (2 g, 0.0041 mol) was dissolved in $POCl_3$ (5 ml) and stirred at room temperature for 30 min. The mixture was slowly heated to reflux and refluxed for 3 h. Excess of $POCl_3$ was evaporated and water 50 ml and methanol (5 ml) were carefully added to the residue. The mixture was stirred at room temperature until all material was dissolved. The pH of the water was adjusted to 10-11 by addition of NaOH followed by extraction with toluene 2×50 ml. The organic layer was separated and evaporated to give a dark residue of 11-(4-[2-(2-acetyloxy-ethoxy)ethyl]-1-piperazinyl]dibenzo[b,f]-1,4-thiazepine (1.53 g).

$^1$H NMR (CDCl3): 2.06 (3H, s), 2.52-2.67 (5H, m), 3.46-3.68 (8H, m), 4.21 (2H, m), 6.68 (1H, t), 7.06 (1H, d), 7.16 (1H, t), 7.31 (3H, m), 7.38 (2H, d), 7.50 (1H, d).
$^{13}$C NMR (CDCl3): 20.9, 46.7, 47.6, 53.4, 57.8, 63.4, 68.9, 70.0, 122.8, 125.3, 128.0, 128.2, 129.0, 129.1, 130.7, 132.1, 132.2, 134.2, 140.0, 148.9, 160.7, 171.0.

e. Quetiapine Base

The residue of 11-(4-[2-(2-acetyloxyethoxy)ethyl]-1-piperazinyl]dibenzo[b,f]-1,4-thiazepine (7.8 g) was dissolved in ethanol (50 ml) and 1M NaOH solution (55 ml) was added. The mixture was stirred at room temperature for 30 min. The product was extracted into toluene (2×100 ml). Evaporation of the toluene phase gave quetiapine base (6.9 g).

Example 2

Steps a and b as in Example 1 c. Dihydrobromide salt of [2-(2-amino-phenylsulfanyl)-phenyl-{4(2-(2-hydroxyethoxy)ethyl]piperazin-1-yl}methanone The evaporation residue of [2-(2-amino-phenylsulfanyl)-phenyl-{4(2-(2-hydroxyethoxy)ethyl]piperazin-1-yl}methanone (example 2) (7.5 g, 0.019 mol) was dissolved in 2-propanol (40 ml). The mixture was heated to 80° C., and a 34% solution of HBr in AcOH (9.3 g, 2.1 mol) was slowly added to the almost refluxing mixture. The solution was slowly allowed to reach room temperature and finally kept 30 min in an ice water bath. The precipitated product was filtered and washed with cold 2-propanol to afford the dihydrobromide as a pale grey powder (7.4 g).

d. [2-(2-aminophenylsulfanyl)-phenyl-{4(2-(2-acetoethoxy)ethyl]piperazin-1-yl}methanone×2 HBr Compound [2-(2-amino-phenylsulfanyl)-phenyl-{4(2-(2-hydroxyethoxy)ethyl]piperazin-1-yl}methanone×2 HBr (5 g, 0.009 mol) was dissolved in acetic acid and heated until all solid material was dissolved. Acetic anhydride (0.96 ml, 0.010 mol) was slowly added to the warm reaction mixture at ca. 50° C. The reaction was continued for 2 h at constant temperature. After 2 h the reaction mixture was evaporated to give a dark blue oil (7.3 g) which still contained some acetic acid. HPLC from the residue showed 95% pure [2-(2-amino-phenylsulfanyl)-phenyl-{4(2-(2-acetoxyethoxy)ethyl]piperazin-1-yl}methanone×2 HBr, and it was used without further purification.

Ring closure and deprotection may be carried out in accordance with steps d and e of example 1.

The invention claimed is:
1. A method for the preparation of the compound of formula I or a salt thereof:

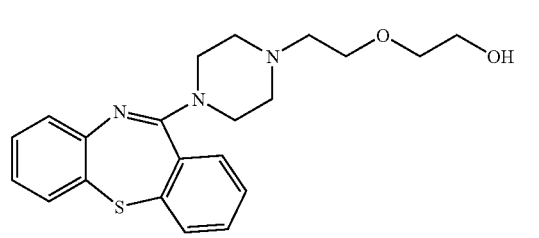

by cyclization of a compound of formula II or a salt thereof:

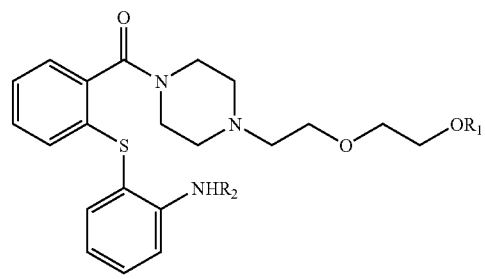

wherein $R_1$ is a hydroxyl protecting group selected from the group consisting of acetyl, benzoyl, pivaloyl, benzyl, 4-methoxybenzyl, allyl, tetrahydropyranyl, silyl, alkyl carbonate, aryl carbonate, aralkyl carbonate, benzyl carbonate, allylsulfonyl, benzylsulfonyl, and toluenesulfonyl, and $R_2$ is H or a suitable amino protecting group to produce a compound of formula III or a salt thereof:

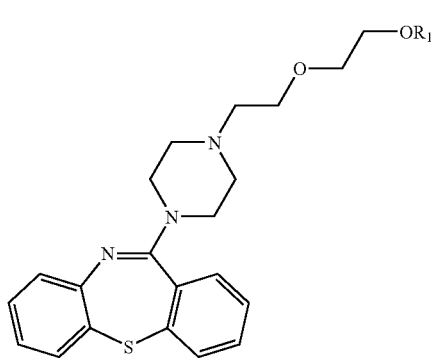

in which $R_1$ is defined as above, which on removal of $R_1$, yields the compound of formula I or a salt thereof.

2. The method of claim 1, wherein compound of formula I is further reacted to a pharmaceutically acceptable salt thereof.

3. The method of claim 1, wherein the cyclization is carried out using phosphorus oxychloride.

4. The method of claim 1, wherein the compound of formula II or a salt thereof is obtained by coupling of 2-aminothiophenol with a compound of formula IV or a salt thereof:

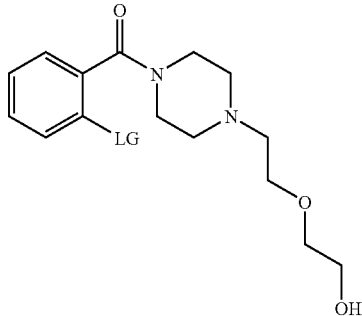

wherein LG represents halogen, diazonium, trifluoromethyl, O-p-toluenesulfonyl, O-trifluoromethanesulfonyl or O-methanesulfonyl, and reacting the resulting intermediate with at least one reagent providing at least the protective group $R_1$, and optionally $R_2$.

5. The method of claim 1, wherein $R_2$ is the suitable amino protecting group selected from the group consisting of acetyl, pivaloyl and benzyl.

* * * * *